Figure 1A:
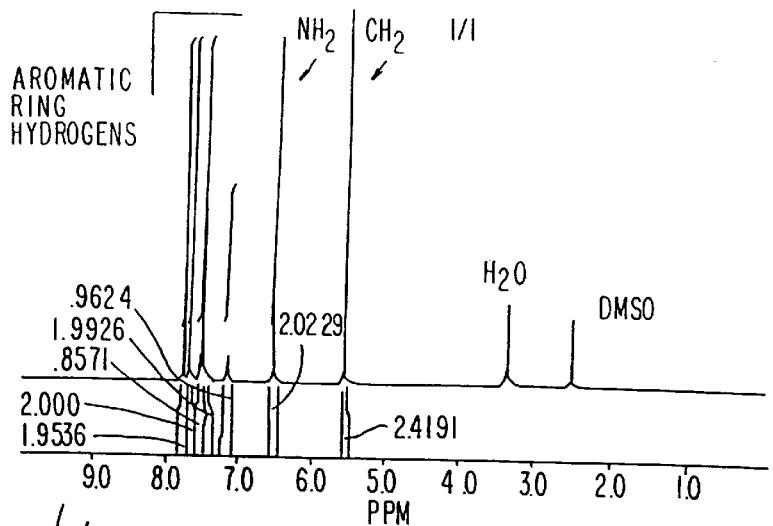

United States Patent [19]

Wehrmann

[11] Patent Number: 5,912,346
[45] Date of Patent: Jun. 15, 1999

[54] TREATMENT AND PREVENTION OF NEOPLASMS WITH SALTS OF AMINOIMIDAZOLE CARBOXAMIDE AND 5-AMINO OR SUBSTITUTED AMINO 1,2,3-TRIAZOLES

[75] Inventor: Felix Wehrmann, Vienna, Austria

[73] Assignee: Constantia Gruppe, Weiner, Austria

[21] Appl. No.: 08/966,066

[22] Filed: Nov. 10, 1997

Related U.S. Application Data

[60] Division of application No. 08/684,297, Jul. 18, 1996, which is a continuation-in-part of application No. 08/505,439, Jul. 21, 1995, Pat. No. 5,728,707.

[51] Int. Cl.$^6$ ...................... C07D 239/22; C07D 249/02; C07D 249/04
[52] U.S. Cl. .......................... 544/310; 548/255
[58] Field of Search ........................ 544/310; 548/255; 514/274, 359

[56] References Cited

U.S. PATENT DOCUMENTS

| | | | |
|---|---|---|---|
| 4,590,201 | 5/1986 | Bochis et al. | 514/359 |
| 4,752,611 | 6/1988 | Graham | 514/359 |
| 4,923,885 | 5/1990 | Hupe et al. | 514/359 |
| 5,132,315 | 7/1992 | Kohn et al. | 514/359 |
| 5,359,078 | 10/1994 | Kohn et al. | 548/255 |
| 5,498,620 | 3/1996 | Kohn et al. | 514/359 |

OTHER PUBLICATIONS

Al–Safi, S.A., and Maddocks, J.L., 1984, "Azathioprine and 6–mercaptopurine (6–MP) suppress the human mixed lymphocyte reaction (MLR) by different mechanisms", Br. J. Clin. Pharmac. 17:417–422.

Bonadonna, G., and Valagussa, P., 1988, "Adjuvant chemotherapy for breast cancer", Semin. Surg. Oncol. 4:250–255.

DeVita, V.T., et al., 1975, "Combination versus single agent chemotherapy: A review of the basis for selection of drug treatment of cancer", Can 35:98–110.

Frei, III, E., 1972, "Combination cancer therapy: Presidental address", Cancer Res. 32:2593–2607.

Hakala et al., 1964, "Prevention of the growth–inhibitory effect of 6–mercaptopurine by 4–aminoimidazole–5–carboxamide" Biochim Biophys Acta 80:665–668.

Hano, K., and Akashi, A., 1964, "Influences of anticancer agents on the metabolism of 8–aminolevulinic acid in normal and tumor–bearing mice", Gann 55:25–40.

Harris, C.C., 1979, "A delayed complication of cancer therapy—cancer", J. Natl. Cancer Inst. 63:275–277.

Horrobin, D.F., et al., 1978, "Thromboxane A2: A key regulator of prostaglandin biosynthesis and of interactions between prostaglandins, calcium and cyclic nucleotides", Med. Hypothesis 4:178–186.

Karmali, R.A., 1983, "Prostaglandins and cancer", CA Cancer J. Clin. 33:322–332.

Karmali, R.A., et al., 1993, "Plant and marine n–3 fatty acids inhibit experimental metastasis of rat mammary adenocarcinoma cells", Prost. Leuk. Essential & Fatty Acids 48:309–314.

Kohn E.C. et al., 1990, J. Nat Cancer Inst. 82:54–60.

Kohn E.C. et al., 1992, Cancer Res. 52:3208–3212.

Myers, C.E., 1992, "Anthracyclines", Cancer Chemother. Biol. Response Modif. 13:45–52.

Rutty, C.J., et al., 1984, "the species dependent pharmacokinetics of DTIC", Br. J. Cancer 48:140.

Shealy, Y.F., and Kranth, C.A., 1966, "Imidazoles. II.5(or 4)–(monosubstituted triazeno)imidazole–4(or 5)–carboxamides", J. Med. Chem. 9:34–38.

Shealy, Y.F., et al., 1962, "Imidazoles. I. Coupling reactions of 5–diazoimidazole–4–carboxamide", J. Org. Chem. 27:2150–2154.

Shealy, Y.F., et al., 1961, "Synthesis of potential anticancer agents. XXIX. 5–Diazoimidazole–4–carboxamide and 5–Diazo–v–triazole–4–carboxamide" J. Org. Chem. 26:2396–2401.

Shealy, Y.F., et al., 1962, "Antitumor activity of triazenoimidazoles", Biochem. Pharmacol. 11:674–676.

Terao, S., et al., 1985, "Thromoxane synthetase inhibitors: Design and synthesis of a novel series of w–pyridylalkenoic acid", Advances in Prostagl. Thromb. Leuk Res. 15:315–317.

Weiss, R.B., and DeVita, Jr., V.T., 1979, "Multimodal primary cancer treatment (Adjuvant chemotherapy): Current results and future prospects", Ann. Intern. Med. 91:251–260.

*Primary Examiner*—Richard L. Raymond
*Attorney, Agent, or Firm*—Stroock & Stroock & Lavan LLP

[57] ABSTRACT

Methods and compositions for the prevention and/or inhibition of primary and secondary metastatic neoplasms are described. Individuals at a high risk of developing neoplasia and/or cancer patients undergoing conventional therapies may be treated with an effective dose of a salt of aminoimidazole carboxamide and/or of 5-amino or substituted amino 1,2,3-traizoles.

7 Claims, 1 Drawing Sheet

L651582

OROTIC ACID

L651582 OROTATE

TREATMENT AND PREVENTION OF NEOPLASMS WITH SALTS OF AMINOIMIDAZOLE CARBOXAMIDE AND 5-AMINO OR SUBSTITUTED AMINO 1,2,3-TRIAZOLES

The application is a divisional of application Ser. No. 08/684,297, filed Jul. 18, 1996, for TREATMENT AND PREVENTION OF NEOPLASMS WITH SALTS OF AMINOIMIDAZOLE CARBOXAMIDE AND 5-AMINO OR SUBSTITUTED AMINO 1, 2, 3-TRIAZOLES, which is a continuation-in-part of application Ser. No. 08/505,439, filed Jul. 21, 1995, now U.S. Pat. No. 5,728,707.

1. INTRODUCTION

The present invention is directed to compositions and methods for the prevention and/or inhibition of primary and secondary metastatic neoplasms by treatment with salts of aminoimidazole carboxamide (AICA) and of 5-amino or substituted amino 1,2,3-triazoles (TRIAZOLES). Use of the entire group of organic acid salts and inorganic salts of 5-aminoimidazole carboxamide and/or of 5-amino or substituted amino 1,2,3-triazoles rather than only those obtained from orotic acid are encompassed by the methods of the invention. For example, AICA and/or TRIAZOLES may also be reacted with aliphatic acids including but not limited to, lactic, succinic, maleic, citric, and tartaric or with sugar acids such as gluconic, galactonic, etc., particularly penta and poly hydroxycarboxylic acids to form organic acid salts, or AICA and/or TRIAZOLES may be reacted with inorganic acids including but not limited to, hydrochloric and phosphoric acids, to form inorganic salts suitable for use according to the methods of the present invention. The methods involve treating an individual at enhanced risk for cancer and/or suffering from cancer with a therapeutically effective dose of a salt of aminoimidazole carboxamide and/or salt of 5-amino or substituted amino 1,2,3-triazoles. In the practice of the cancer treatment method of the invention, compositions containing salts of AICA and/or TRIAZOLES are used to inhibit the development and proliferation of cancer cells at the primary and secondary sites and cells of the surrounding stromal tissues. Preferred compositions of the invention are those which specifically or preferentially prevent transformation of preneoplastic cells to tumor cells, and prevent or inhibit tumor cell proliferation, invasion and metastasis without general cytotoxic effects. The methods further involve treating individuals with disease conditions including, but not limited to, psoriasis, eczema, collagen vasculitides, neurologic diseases or drug toxicity.

2. BACKGROUND OF THE INVENTION

2.1 SALTS OF AMINOIMIDAZOLE CARBOXAMIDE

AICA is referred to as "Orazamide" in the literature. Orazamide, a salt of aminoimidazole carboxamide (hereinafter referred "AICA"), has been used as a hepatoprotectant based on its ability to prevent necrosis and stimulate regeneration of the liver parenchymal cells.

2.1.1 CHEMICAL NATURE AND PROPERTIES OF SALTS OF AMINOIMIDAZOLE CARBOXAMIDE

Orazamide is available in different forms as: 5-aminoimidazole-4-carboxamide orotate, 4-amino-5-imidazole carboxamide orotate or a combination of 1,2,3,6-tetrahydro-2,6-dioxo-4-pyrimidine carboxylic acid with 5-amino-1H-imidazole-4-carboxamide (1:1) or a combination of orotic acid with 5(or 4)-aminoimidazole-4(or 5)-carboxamide (1:1). The $C_5$ amine group on the imidazole ring can be attached to the $C_4$ carboxyl group of orotic acid or any other organic acid which is chemically compatible with the body.

The known pharmacological activity of AICA orotate or orazamide resides in AICA and/or orotic acid. AICA is incorporated into animal nucleic acids, especially in purine biosynthesis. Orotic acid, also found in milk, is a pyrimidine precursor in animal organisms. Thus, AICA orotate contains precursors of purine and pyrimidine components of nucleic acids and its application as a hepatoprotectant was based on its stimulatory effects on regeneration of liver parenchymal cells.

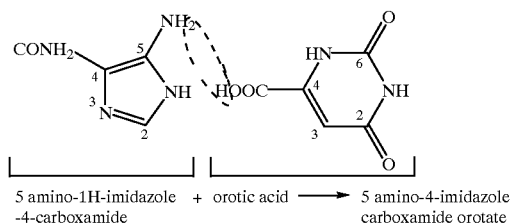

5-amino-1H-imidazole    +  orotic acid  ⟶    5 amino-4-imidazole
-4-carboxamide                                carboxamide orotate

2.1.2 PHARMACOKINETICS OF AICA SALTS

Orazamide or AICA orotate is currently used as a hepatoprotectant. AICA has been found to prevent liver necrosis and stimulate regeneration of the liver parenchymal cells. Upon administration of an AICA salt, AICA is the major metabolite.

2.1.3 AICA SALTS AND CANCER

The observation that AICA is utilized as a precursor in purine biosynthesis by normal and tumor cells suggested that an analog of AICA may exert an antitumor activity by inhibiting the biosynthetic pathway to nucleic acids. Hano, K., and Akashi, A., 1964, *Gann* 55:25–35. Therefore, a series of triazenoimidazoles, analogs of AICA in which the 5-amino group has been replaced by various monoalkyl- and dialkyltriazeno groups, has been synthesized and evaluated for antitumor activity. Shealy, Y. F., and Kranth, C. A., 1966, *J. Med. Chem.* 9:34–38, Shealy, Y. F., et al., 1962, *J. Org. Chem.* 27:2150–2154; and Shealy, Y. F., et al., 1961, *J. Org. Chem.* 26:2396–2401. One of these analogs, 5-(dimethyltriazeno) imidazole-4-carboxamine (DTIC or DTIC-Dome, Dacarbazine), having the following formula:

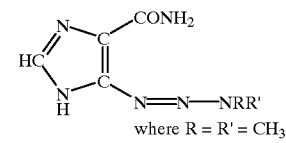

where R = R' = CH$_3$ has exhibited notable activity against mouse sarcoma 180, adenocarcinoma 755, leukemia L1210 (Shealy, Y. F., et al., 1962, *Biochem. Pharmacol.* 11:674–676) and melanoma cells, (Rutty, C. J., et al., 1984, *Br. J. Cancer* 48:140).

Dacarbazine or DTIC-Dome is used as an anticancer agent in humans. After intravenous administration of DTIC-Dome, the volume of distribution exceeds total body water content suggesting localization in some body tissue, probably the liver. Its disappearance from the plasma is biphasic with an initial half-life of 19 minutes and a terminal half-life of 5 hours. The average cumulative excretion of unchanged DTIC in the urine is 40% of the injected dose in 6 hours. DTIC is subject to renal tubular secretion rather than glomerular filtration. At therapeutic concentrations DTIC is not appreciably bound to human plasma protein. DTIC is degraded extensively in man. Besides unchanged DTIC, 5-aminoimidazole-4-carboxamide (AICA) is the major metabolite of DTIC excreted in the urine. AICA is not derived endogenously, but from the injected DTIC, because the administration of radioactive DTIC labeled with $^{14}$C in the imidazole portion of the molecule (DTIC-2-$^{14}$C) gives rise to AICA-2-$^{14}$C. Although the exact mechanism of action of DTIC-Dome is not known, three hypotheses have been offered: 1) inhibition of DNA synthesis by acting as a purine analog; 2) action as an alkylating agent; and 3) interaction with SH groups. DTIC-Dome is indicated in the treatment of metastatic malignant melanoma. In addition, DTIC-Dome is also indicated for Hodgkin's disease as a secondary-line therapy when used in combination with other effective agents.

Even though AICA is the major metabolite of DTIC, there is no suggestion in the prior art nor any evidence to indicate whether the AICA formed is important in bringing about the anti-tumor and/or antimetastatic effect of DTIC-Dome. There is no prior art to suggest that DTIC-Dome may be a prodrug for AICA. The term "prodrug" as used herein describes pharmacologically inactive chemical derivatives of a drug molecule that require a transformation within the body in order to release the active drug. In fact, analogs of AICA such as DTIC-Dome were developed with the objective of blocking and/or competing with AICA and interfering with the synthesis of nucleic acids. In this regard, there is one report by Hakala et al., 1964, *Biochem. Biophys. Acts.* 80:666–668, indicating that AICA prevented the growth inhibitory effects of the chemotherapeutic agent, 6-mercaptopurine on tumor cells in vitro. However, in this connection, it has also been reported that AICA has been found to be able to prevent 6-mercaptopurine induced suppression of lymphocyte responsiveness in vitro. Al-Safi, S. A., and Maddocks, J. L., 1984, *Br. J. Clin. Pharmac.* 17:417–422. In addition, AICA was found to exhibit an antioxidant activity and increase the superoxide dismutase expression in lymphocytes incubated in vitro. Muzes, G., et al., 1990, *Acta Physiologica Hungarica* 76:183–190. The use of AICA alone or in combination with a cancer chemotherapeutic agent has not been reported for the prevention and treatment of primary and metastatic neoplastic diseases and other diseases.

2.2 SALTS OF 5-AMINO OR SUBSTITUTED AMINO 1,2,3-TRIAZOLES 5-amino or substituted amino 1,2,3-triazoles were originally disclosed as having anticoccidial activity in poultry (U.S. Pat. No. 4,590,201, issued May 20, 1986), and later as cancer treatment agents in the treatment of peritoneal carcinomatosis of ovarian cancer (U.S. Pat. No. 5,132,315, issued Jul. 21, 1992 and Kohn E. C. et al., 1990, *J. Natl Cancer Inst.* 82:54–60) and as antimetastatic agents in the PMT-6 fibrosarcoma tumor model in mice (U.S. Pat. No. 5,045,543, issued Sep. 3, 1991). One 1,2,3-triazole-4-carboxamide compound in particular, 5-amino-1-(4-[4-chlorobenzoyl]-3,5-dichlorobenzyl-1,2,3-triazole-4-carboxamide, designated L651582 (Merck Research Laboratories, U.S. Pat. No. 4,590,201) and having the following formula:

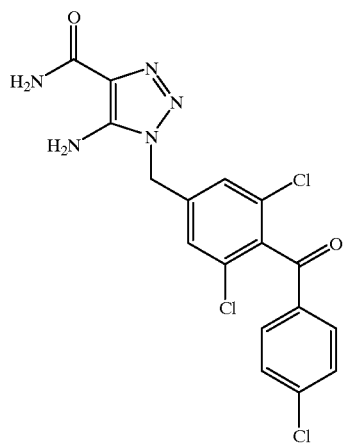

was also shown to inhibit cell proliferation, inflammation and some signal transduction pathways including those which involve calcium influx, the release of arachidonic acid and the generation of inositol phosphates. Kohn, E. C. et al., 1992, *Cancer Res.* 52:3208–3212 and Felder, et al., 1991, *J. Pharmacolol. Exp. Ther.* 257:967–971.

Arachidonic acid and/or its eicosanoid metabolites have been implicated in different stages of malignancies and a large variety of diseases including, but not limited to, psoriasis, eczema, systemic lupus erythematosus or arthritis. Pharmacologic inhibition of eicosanoid synthesis in animal models and humans has resulted in inhibition of development and progression of cancer and other diseases. Karmali, R. A., et al., 1982, Prostaglandins and Med 8:437–446; and Karmali, R. A., et al., 1985, Prostaglandins Leuk Med 20:283–286. L651582 has been demonstrated to inhibit arachidonic acid release thereby reducing the amount of substrate available for eicosanoid synthesis. To date, no studies have been reported on efficacy of salts of L651582 or its related compounds.

2.3 METABOLIC EFFECT OF OROTIC ACID

Any kind of organic or inorganic acid which is clinically compatible with the body may be selected to be reacted with AICA or 5-amino or substituted amino 1,2,3-triazoles. Especially desirable are orotic, lactic, succinic, maleic, citric, tartaric, gluconic, galactonic, hydrochloric, phosphoric and penta or poly hydroxycarboxylic acids.

Orotic acid is an intermediate in the pyrimidine pathway and its main source in the human and animal diet is bovine milk and its products. Orotic acid inhibited stimulation of protein synthesis and reduced the activity of ornithine decarboxylase, an enzyme which is believed to be a valuable index of cell proliferation. Grezelkowska K., et al., 1993, *Endocrine Regulations* 27:133–138. However, an orotate salt of AICA and/or 5-amino or substituted amino 1,2,3-triazoles has not been described for the prevention and treatment of neoplastic or other diseases.

2.4 CANCER GROWTH AND CHEMOTHERAPY

Cancer is a disease of inappropriate tissue accumulation. This derangement is most evident clinically when tumor tissue bulk compromises the function of vital organs. Contrary to what is generally thought, human malignant disorders are usually not diseases of rapid cell proliferation. In fact, the cells of most common cancers proliferate more slowly than many cells in normal tissues. It is a relatively slow accumulation of tumor tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity. Understanding the use of chemotherapy requires a comprehension of both the drugs' mechanisms of action and the pathophysiology of cancer, which is rooted in deranged cellular and tissue growth.

Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumors are composed mostly of noncycling cells, it is not surprising that chemotherapy is not always effective in eradicating cancer.

The strategy of cancer treatment is to shift tumor cells from a noncycling compartment to a cycling compartment. Several methods that promote this shift form the basis for combined-modality treatment. Surgery is most commonly used to reduce tumor size and thus facilitate reentry of cancer cells into the cell cycle. After a primary tumor is completely removed, microscopic metastases may remain at distant sites. Because of their small size, the micrometastases are composed principally of cycling cells. Small numbers of cells that remain at the primary tumor site are also likely to reenter the cell cycle. Thus, the remaining cancer cells are often susceptible to chemotherapy. Radiation therapy or chemotherapy alone can also be used to reduce tumor bulk and thus recruit cells into the cycling cell compartment. For example, the strategy of adjuvant chemotherapy for breast is based on these concepts. Weiss, R. B., and DeVita, Jr., V. T., 1979, *Ann. Intern. Med.* 91:251; Bonadonna, G., and Valagussa, P., 1988, *Semin. Surg. Oncol.* 4:250.

2.4.1 COMBINED CHEMOTHERAPY

Animal tumor investigations and human clinical trials have shown that drug combinations produce higher rates of objective response and longer survival than single agents. Frei, III, E., 1972, *Cancer Res.* 32:2593–2607. Combination drug therapy is, therefore, the basis for most chemotherapy employed at present. Combination chemotherapy uses the different mechanisms of action and cytotoxic potentials of multiple drugs. Although all chemotherapeutic drugs are most effective on cells that are synthesizing DNA, many agents—particularly the alkylating agents—can kill cells that are not cycling. Such agents are termed non-cell proliferation-dependent drugs. Some agents, including many of the antimetabolites and antibiotics, are most active against cells during DNA synthesis and are, therefore, termed cell-proliferation-dependent drugs. Repetitive administration of non-cell-proliferation-dependent agents can shrink tumor mass by killing cells in both the cycling and noncycling compartments of the tumor; the surviving cells will then move into the cycling compartment, where they are more susceptible to cell proliferation-dependent drugs. The combined use of agents less dependent on the cell cycle followed by those dependent on cell proliferation enhances tumor cell death. Each cycle of treatment kills a fixed fraction of cells, so repetitive cycles are required for cure. For example, a drug combination that kills 99.9 percent of cancer cells per treatment cycle would have to be repeated at least six times to eliminate an average tumor burden, if tumor cells did not regrow between cycles.

Several principles guide the selection of drugs to be used in combination. Drugs that are active individually are combined and administered in the highest doses the patient can tolerate and given as frequently as toxicity allows; drug combinations with limited overlaps of major toxicities are therefore preferable. The drugs selected should also have different mechanisms of action. This approach enhances cancer cell kill, reduces the chance that drug resistant cell populations will emerge, and disrupts cancer cell function by attacking multiple metabolic pathways. DeVita, V. T., et al., 1975, *Cancer* 35:98. However, even though the chemotherapeutic agents are more effective in killing or damaging malignant cells than normal cells, the fact that they do harm normal cells indicates their great potential for toxicity. For chemotherapy to be effective, the patient must be in good physiologic condition.

2.4.2 STRATEGIES IN THE USE OF CHEMOTHERAPY

Cancer treatment requires inhibition of a variety of factors including tumor cell proliferation, metastatic dissemination of cancer cells to other parts of the body, invasion, tumor-induced neovascularization, and enhancement of host immunological responses and cytotoxicity. Conventional cancer chemotherapeutic agents have often been selected on the basis of their cytotoxicity to tumor cells. However, some anticancer agents have adverse effects on the patient's immunological system. Unfortunately, for the vast majority of conventional antineoplastic agents the margin between an effective dose and a toxic dose, i.e., the therapeutic index, is extremely low. Thus, it would be greatly advantageous if a cancer therapy or treatment could be developed that would afford noncytotoxic protection against factors that might lead to growth, progression and metastasis of invasive cancers.

2.5 DISEASES CHARACTERIZED BY ABNORMAL CELL PROLIFERATION

A number of clinical disease conditions are characterized by abnormal cell proliferation, e.g., psoriasis, eczema and endometriosis which result from localized spread of diseased cells. Other diseases associated with abnormal cell proliferation include, but are not limited to, systemic lupus erythematosus, arthritis, nerve conduction diseases and cystic fibrosis.

3. SUMMARY OF THE INVENTION

The present invention is directed to a method for the prevention and/or treatment of primary and metastatic neoplasms which involves using a salt of AICA to treat a patient suffering from a cancer. Accordingly, an effective dose of an AICA salt is administered to an individual suffering from cancer.

The present invention is also directed to an improved method for the prevention and/or treatment of primary and metastatic neoplasms which involves using a salt of 5-amino or substituted amino 1,2,3-triazoles, a class of compounds of the formula:

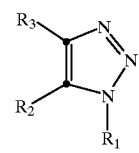

wherein,

R₁ is —(CH₂)ₚ— 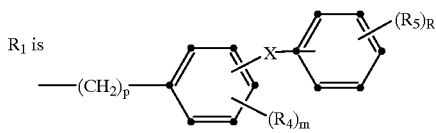

wherein p is 0 to 2; m is 0 to 4; and n is 0 to 5; X is O, S, SO, SO₂, CO, CHCN, CH₂ or C=NR₆ where R₆ is hydrogen, loweralkyl, hydroxy, loweralkoxy, amino, loweralkylamino, diloweralkylamino or cyano; and, R₄ and R₅ are independently halogen, cyano, trifluoromethyl, loweralkanoyl, nitro, loweralkyl, loweralkoxy, carboxy, lowercarbalkoxy, trifuloromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; R₂ is amino, mono or diloweralkyl amino, acetamido, acetimido, ureido, formamido, formimido or guanidino; and R₃ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atoms.

In particular, the composition of the present invention includes, but is not limited to a salt of L651582 or 5-amino-1-(4-[4-chlorobenzoyl]-3,5-dichlorobenzyl)-1,2,3-triazole-4-carboxamide, to treat a patient suffering from a cancer. Accordingly, an effective dose of a salt of 5-amino or a substituted amino 1,2,3-triazole compound is administered to an individual suffering from a cancer.

The salts of 5-amino or a substituted amino 1,2,3-triazole compound used in the methods of this invention are novel and constitute another aspect of the invention. A preferred embodiment of the present invention is the orotate salt of L651582 or the orotate salt of 1,2,3-triazole-4-carboxamide.

The present invention is also directed to a method of evaluating susceptibility of a cancer to growth inhibition with a salt of AICA or of a 5-amino or a substituted amino 1,2,3-triazole compound.

The present invention is also directed to a method for the prevention and/or treatment of metastatic neoplasms which involves using an effective dose of a combination of an AICA salt and/or a salt of 5-amino or a substituted amino 1,2,3-triazole compound, with or without conventional chemotherapy or hormonal and/or radiation therapy or surgery, to treat a patient suffering from cancer.

The present invention is also directed to a method for preventing immunosuppression and toxicity induced by anticancer chemotherapeutic agents or for inducing immunostimulation in a patient suffering from cancer, which involves using an effective does of an AICA salt or a salt of 5-amino or a substituted amino 1,2,3-triazole compound. The preferred embodiment of an AICA salt is AICA hydrochloride or AICA orotate. The preferred embodiment of a salt of a triazole compound is orotate salt of L651582 or 5-amino-1-(4 -[4-chlorobenzoyl]-3,5-dichlorobenzyl)-1,2,3,-triazole-4-carboxamide.

The method of the invention relates to therapeutic protocols for treatment of cancer using salts of AICA or of 5-amino or a substituted amino 1,2,3-triazole compound, and an acid including, but not limited to, orotic acid, aliphatic acids such as lactic, succinic, maleic, citric and tartaric or with sugar acids such as gluconic and galactonic, particularly penta and poly hydrocarboxylic acids to form organic acid salts. AICA or 5-amino or a substituted amino, 1,2,3-triazole compound may also be reacted with inorganic acids including, but not limited to, hydrochloric acid and phosphoric acid to form inorganic salts. The preferred method of the invention relates to therapeutic protocols for treatment of different types of cancer using AICA orotate or AICA hydrochloride as an adjuvant chemotherapeutic agent. An additional preferred embodiment of the invention relates to therapeutic protocols for treatment of different types of cancer using the orotate or chloride salt of L651582 (5-amino-1-(4-[4-chlorobenzoyl]-3,5-dichlorobenzyl)-1,2,3-triazole-4-carboxamide) as an adjuvant chemotherapeutic agent.

The present invention further provides methods for using salts of AICA or of 5 amino or a substituted amino 1,2,3-triazole compound to treat diseases involving abnormal cell proliferation including but not limited to, psoriasis, eczema, collagen, vasculitides, neurologic diseases or drug toxicity.

4. DETAILED DESCRIPTION OF FIGURES

Figure 1B:
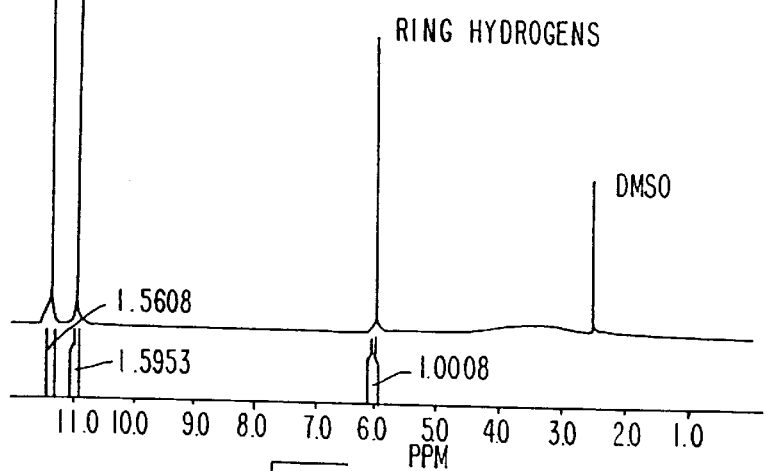
Figure 1C:
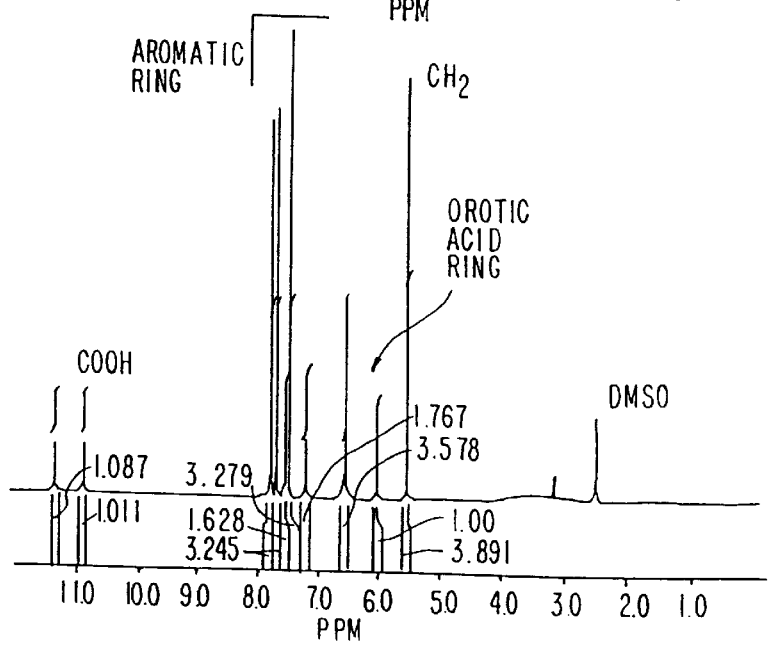

FIG. 1 illustrates proton NMR Scans of L651582, orotic acid and L651582 orotate. The orotate salt of L651582 is dissolved in DMSO.

5. DETAILED DESCRIPTION OF THE INVENTION

The method of the invention involves administering an effective dose of an organic acid salt or inorganic acid salt of AICA or a salt of 5-amino or a substituted amino 1,2,3-triazole, to an individual who is identified as being at enhanced risk for cancer and/or as having cancer, in order to treat and prevent primary and/or metastatic cancer.

It will be apparent to those skilled in the art that other salts of AICA or TRIAZOLE-related compounds which inhibit cancer cell proliferation and spread may be useful as therapeutic agents. Such additional compounds may be identified using growth-inhibition assays described herein.

It may be that the ability of AICA or TRIAZOLE salts to inhibit tumor cell proliferation, to inhibit the metastatic dissemination of tumor cells, to induce immunostimulation and/or to prevent immunosuppression induced by some chemotherapeutic agents used in cancer patients, contributes to the efficacy or effectiveness for use in the treatment and prevention of primary and secondary neoplasms. These possible mechanisms of action are in no way meant to limit the scope of the invention and are presented purely for explanatory and/or illustrative purposes.

For example, the most life-threatening aspect of cancer is the uncontrolled growth and undetected spread of cancer cells (metastasis) throughout the body.

5.1 PATHOBIOLOGY OF INVASION AND METASTABIS

The two essential features of cancer are invasion and metastasis. At one extreme, microinvasion of the basement membrane characterizes the transition from neoplasia to cancer, and at the other extreme, metastases generally lead to death.

Invasion into the underlying connective tissue by the primary tumor proceeds in stages and is facilitated by various mediators produced by the tumor cells. Tumor cells that have not invaded the basement membrane and remain confined within the epithelium are termed carcinoma in situ. Release of collagenase IV by these cells dissolves the collagen in the basement membrane and allows the tumor to penetrate the subjacent stroma. Invasive tumor cells carry membrane receptors for laminin and fibronectin, large glycoprotein components of the basement membrane and connective tissue stroma, respectively. Binding to these elements provides the tumor cells with a lattice for anchorage and advancement. Enzymes released by tumor cells, such as plasminogen activators, collagenases I, II and III, cathepsins, heparanase and hyaluronidase, destroy matrix constituents, including fibrin, glycoproteins, proteoglycans and hyaluronic acid, thus enabling the cells to advance further into the connective tissue. Tumors also secrete inflammatory mediators such as eicosanoids, prostaglandins, free radical oxidants and oxidative adducts, and autocrine motility factors, which direct the motion of the advancing tumor, vascular permeability factors which allow plasma proteins to accumulate in the tumor, and angiogenic factors which increase the vascularity of the tumor. Tumor cells preferentially invade along pathways that provide the least resistance, such as the connective tissue stroma. Tumors are much less likely to invade resistant tissue such as fascia, bone or thick-walled arteries and arterioles. However, they readily penetrate the venous capillaries or lymphatics, which have walls composed of a single layer of cells. Because the venous and lymphatic systems are interconnected, tumor cells that enter a lymphatic vessel may become enmeshed in a lymph node or may enter the venous circulation and disseminate to distant sites. As tumors enlarge, the intratumor vascularity may be compromised, thereby leading to hemorrhage and necrosis and a decrease in the growth fraction.

Metastases, on the other hand, may form when circulating tumor cells with adherent lymphocytes and platelets are trapped in capillaries and the tumor cell membrane interacts with the capillary endothelium. The capillary endothelial junctions retract, and tumor cell ligands bind to receptors on the endothelial and basement membranes. Tumor cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumor cells then may proliferate and synthesize platelet aggregatory factors such as thromboxanes and procoagulants, thereby leading to the deposition of a fibrin cocoon around the cells. Such a cocoon may protect the micrometastasis from attack by the host's immune system.

Some experimental tumors in animals and most spontaneous human tumors are accompanied by increased concentrations of local and circulating eicosanoids, prostaglandins, free radical oxidants, oxidative adducts, immunosuppression, bone metastasis, and hypercalcemia. Since prostaglandin E2 has immunosuppressive and osteolytic activities, PGE2 has been implicated in such paraneoplastic symptoms. Karmali, R. A., 1983, *CA Cancer J Clin.* 33:322–332. Some studies have implicated platelet aggregation and the effects of prostaglandins thereon in the hematogenous metastasis of tumors. There is evidence that platelets play an important role in metastatic dissemination of cancer cells. Tumor cells display specific properties towards platelets and the vascular endothelium. Platelet aggregation is induced by tumor cells, and aggregating platelets elaborate growth factors that promote tumorigenesis.

Since the aggregation of platelets requires production of lipid peroxides and/or thromboxane from arachidonic acid metabolism, improved understanding of how thromboxane $A_2$ inhibition is achieved can be expected to exert antimetastatic effects. Inhibition of thromboxane $A_2$ synthesis by eicosapentaenoic acid inhibited experimental metastasis of mammary adenocarcinoma cells in rats. Karmali et al., 1993, *Prost. Leuk. Essential & Fatty Acids* 48:309–314. Thromboxane $A_2$ synthesis can be inhibited by imidazole compounds, e.g., aminoimidazole carboxamide. Horrobin, D. F., et al., 1978, *Med. Hypothesis* 4:178–184; and Terao, S., et al., 1985, *Advances in Prostagl. Thromb. Leuk Res.* 15:315–315. In addition, AICA was found to have antioxidant activity and to increase superoxide dismutase activity. Muzes, G. et al., 1990, Acta Physiologica Hungarica 76:183–190.

Similarly, L651582 was shown to inhibit signal transduction pathways including those which involve the release of arachidonic acid, a substrate for eicosanoid synthesis (Kohn, E. C. et al., 1992, *Cancer Res.* 52:3208–3212) and to inhibit peritoneal carcinomatosis of ovarian cancer (U.S. Pat. No. 5,132,315, issued Jul. 21, 1992 and Kohn, E. C. et al., 1990, *J. Natl. Cancer Inst.* 82:54–60).

In the present invention administration of salts of AICA or of 5-amino or substituted amino 1,2,3-triazoles, results in inhibition of eicosanoids and thromboxane $A_2$ and/or enhanced antioxidant defenses against oxidants and free radicals by superoxide dismutases. More specifically, administration of AICA hydrochloride resulted in inhibition of prostatic tumors in rats. However, unexpectedly, administration of an orotate salt of L651582 resulted in a greater inhibition of tumor growth than with L651582. See, infra, Section 7. Thus, novel salts of the 5 amino or substituted amino 1,2,3-triazole compounds of the present invention are disclosed as having improved and greater anticancer activity than L651582. These compounds are useful for the prevention and/or inhibition of primary and secondary metastatic neoplasms.

Pharmaceutical intervention directed to specific lymphocyte functions also offers a new approach to cancer treatment and prevention. For example, tumors are heterogenous tissues containing a supporting stroma that is infiltrated, to varying degrees, with lymphocytes. These tumor-infiltrating lymphocytes have been isolated, activated with interleukin-2 (IL-2) in vitro and used to treat patients with advanced cancers. However, treatment of patients with anti-cancer agents such as chemotherapeutic drugs or ionizing radiation can be very immunosuppressive. Several forms of toxic and drug-induced tissue damage involve free radical mechanisms. Gerson, R. J., et al., 1985, Biochem. Biophys. Res. Commun. 126:1129–1135. Lymphocytes are highly sensitive to destruction by many chemotherapeutic drugs and ionizing radiation. As expected, immunosuppression caused by these agents often leads to increased susceptibility to infection. In addition, many anti-cancer agents are immunosuppressive as well as mutagenic. Induction of a second malignancy may therefore follow successful therapy of the first cancer as a late complication of successful chemotherapy or radiation therapy. Harris, C. C., 1979, *J. Natl. Cancer Inst.* 63:275–277. Most second malignancies originate from the hematopoietic, lymphopoietic and reticuloendothelial systems, which are the most sensitive direct targets of the immunosuppressive anti-cancer agents. For example, some anticancer chemotherapeutic agents such as 6-mercaptopurine have been found to inhibit lymphocyte activity in vitro. It was also found that AICA has been able to prevent the 6-mercaptopurine induced inhibition of lymphocyte activity. Al-Safi, S. A., and Maddocks, J. L., 1984, Br. J. Clin. Pharmac. 17:417–422. Thus, administration of AICA or a salt thereof, along with 6-mercaptopurine can prevent the suppression of lymphocyte responsiveness in vivo. In addition, AICA was found to increase the activity of superoxide dismutases in lymphocytes, thereby providing an effective means to remove highly toxic free oxygen radicals which are often induced by toxic chemotherapeutic agents. Muzes, G., et al., 1990, Acta Physiologica Hungarica 76:183–190.

Along with other signals necessary for immune regulation, cytokines are likely to play a major role in the development of effective cancer immunotherapy. Therefore, AICA salts and salts of 5-amino or substituted 1,2,3-triazoles can be administered in combination with cytokines such as INF-α, IFN-γ, TNF-α, IL-2, IL-4, IL-6 and thymosin α, to stimulate T cell activation in cancer patients for anti-tumor immunotherapy.

5.2. CHOICE OF AICA SALT AND DOSAGE

The present invention provides a number of different organic acid salts of aminoimidazole carboxamide which inhibit tumor cell proliferation and/or metastasis, e.g., 5-aminoimidazole-4-carboxamide orotate or 4-amino-5-imidazolecarboxamide orotate (AICA orotates) or a combination of 1,2,3,6-tetrahydro-2,6-dioxo-4-pyrimidine carboxylic acid compound with 5-amino-1H-imidazole-4-carboxamide (1:1) or a combination of the orotic acid compound with 5(or 4)-aminoimidazole-4(or 5)-carboxamide (1:1); salts of AICA with aliphatic acids such as lactic, succinic, maleic, citric, and tartaric or with sugar acids such as gluconic, galactonic, etc., particularly penta and poly, hydroxycarboxylic acids to form organic acid salts; and inorganic acid salts such as hydrochlorides and/or phosphate salts of AICA suitable for use according to the methods of the present invention.

5.3 CHOICE OF SALT OF 5-AMINO OR A SUBSTITUTED AMINO 1,2,3-TRIAZOLE COMPOUND

The present invention provides novel salts of 5-amino or a substituted amino 1,2,3-triazole compound which inhibit tumor cell proliferation and/or metastasis even greater than the native 5-amino or a substituted amino 1,2,3-triazole compound. The novel salts of the invention involve salts of a class of compounds of the formula:

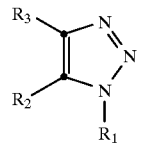

in which an organic acid or an inorganic acid is bonded to $R_2$, wherein, $R_1$ is 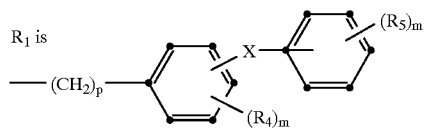

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifuloromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; $R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atoms.

The 5-amino or a substituted amino 1,2,3-triazole compound is reacted with orotic acid, with aliphatic acids including, but not limited to lactic, succinic, maleic, citric and tartaric, or with sugar acids including, but not limited to, gluconic and galactonic, particularly penta and poly hydroxycarboxylic acids, to form organic salts; and inorganic acids including, but not limited to, hydrochloric and phosphonic acid to form salts of 5-amino or a substituted amino 1,2,3-triazole compound suitable for use according to the methods of the present invention.

5.4 DOSAGE AND FORMULATION

AICA salts or salts of 5-amino or substituted amino 1,2,3-triazoles (TRIAZOLE) may be formulated into pharmaceutical preparations for administration to mammals for prevention and treatment of primary and metastatic neoplasms and other cell proliferative diseases.

Many of the AICA or TRIAZOLE salt compounds may be provided as organic acid salts with pharmaceutically compatible counterions, a form in which they are merely water-soluble. Pharmaceutically compatible salts may be formed with many acids, including, but not limited to, aliphatic acids such as lactic, succinic, maleic, citric and tartaric or with sugar acids such as gluconic, galactonic, etc., particularly penta and poly, hydroxycarboxylic acids and inorganic acids including, but not limited to hydrochloric and phosphoric acid. Salts tend to be more soluble in aqueous or other protonic solvents that are the corresponding free base forms.

The therapeutic compounds or pharmaceutical compositions may be administered intravenously, intraperitoneally, subcutaneously, intramuscularly, intrathecally, orally, rectally, topically, or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

Patient dosages for oral administration of AICA salts range from 1–1000 mg/day, commonly 100–300 mg/day, and typically from 200–300 mg/day. Stated in terms of patient body weight, usual dosages range from 0.02 to 12.5 mg/kg/day, commonly from 1.25–3.75 mg/kg/day, typically from 2.5 to 3.75 mg/kg/day. Stated in terms of patient body surface areas, usual dosages range from 0.5–600 mg/m²/day, commonly from 66–200 mg/m²/day, typically from 130–200 mg/m²/day.

Dosage amount and interval may be adjusted individually to provide plasma levels of the active moiety which are sufficient to maintain the anti-proliferative and anti-metastatic effects. Average plasma levels should be maintained with 10–100 microgram/ml, commonly from 10–50 microgram/ml, and typically from 10–20 microgram/ml.

Patient dosages for oral administration of TRIAZOLE salts range from 0.25–250 mg/day, commonly 25–100 mg/day, and typically from 50–100 mg/day. Stated in terms of patient body weight, usual dosages range from 0.005 to 5 mg/kg/day, commonly from 0.25–1.0 mg/kg/day, typically from 0.5 to 1.0 mg/kg/day. Stated in terms of patient body surface areas, usual dosages range from 0.1–150 mg/m²/day, commonly from 20–50 mg/m²/day, typically from 25–50 mg/m²/day.

Dosage amount and interval may be adjusted individually to provide plasma levels of the active moiety which are sufficient to maintain the anti-proliferative and anti-metastatic effects.

Alternatively, one may administer the compound in a local, rather than oral manner, for example, via injection of the compound directly into a tumor, often in a depot or sustained release formulation.

A variety of delivery systems for the pharmacological compounds may be employed, including, but not limited to, liposomes and emulsions. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Furthermore, one may administer the drug in a targeted drug delivery system, for example, in a liposome coated with tumor-specific antibody. The liposomes will be targeted to and taken up selectively by the tumor.

In cases of local administration or selective uptake, the effective local concentration of the drug may not be related to plasma concentration.

5.5 TARGET CANCERS

Cancers that can be prevented and/or treated by the compositions and methods of the present invention include, but are not limited to, human sarcomas and carcinomas, e.g. carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. Specific examples of such cancers are described in the sections below.

5.6 TARGET CELL PROLIFERATIVE DISEASES

Cell proliferative diseases that can be prevented and/or treated by the compositions and methods of the present invention include, but are not limited to, psoriasis, eczema, endometriosis, systemic lupus erythematosus, arthritis, nerve conduction diseases and cystic fibrosis.

5.7. EVALUATION OF ANTI-PROLIFERATIVE ACTIVITY

According to the present invention, assays may be used to determine the susceptibility of particular cell lines to inhibition of proliferation by administering organic acid salts of AICA or TRIAZOLES. Such assays are especially useful in evaluating whether a particular cancer may be treated successfully with an AICA salt or a salt of 5-amino or a substituted amino 1,2,3-triazole compound. This method permits the choice of a therapeutic agent to be tailored to the biochemical characteristics of the individual tumor. The method may be practiced by growing the cancer cell line of interest in multiple sample plates or wells. Some sample plates contain varying concentrations of the test inhibitor so that an $IC_{50}$ may be calculated. The inhibitor-free plates serve as a control. The samples are cultivated for a time sufficient to allow measurable growth. The relative amount of growth in the presence and absence of the test compound is then determined. Cell growth may be measured by any number of methods, such as colony growth in soft agar or incorporation of $^3$H-thymidine. The cancer cell line to be evaluated may be obtained by biopsy of the individual human or animal patient.

Experimental tumor models are used in pre-clinical experimental protocols to determine the susceptibility of particular metastatic and non-metastatic cancers in animals, to inhibition of proliferation and metastasis by administering salts of AICA or TRIAZOLES.

The therapeutic methods of the invention are also directed at inhibiting the growth of non-malignant cells that support the growth and development of the primary neoplasm and/or metastatic lesions. Such non-malignant cells include vascular endothelial cells, other cells of the stroma and benign tumor cells. For example, a solid tumor's requirement for newly formed microvasculature may not be met by inhibiting the growth of vascular endothelial cells.

5.7.1. PROSTATE CANCER

One aspect of the invention relates to the treatment of prostate cancer. Prostate cancer is the second leading cause of death from cancer among men; 25 percent of men with prostate cancer die of the disease. Boring, C. C., et al., 1993, CA Cancer J. Clin. 43:7–26. Moreover, many patients who do not die of prostate cancer require treatment to ameliorate symptoms such as pain, bleeding, and urinary obstruction. Thus, prostate cancer is also a major cause of suffering and of health care expenditures. Catalona, W. J., 1994, New Eng. J. Med. 331:996–1004.

In making decisions about treatment for prostate cancer, clinicians consider the patient's age and general health, the clinical state and histological grade of the cancer, and factors concerning the quality of life, e.g., the immediate risks associated with treatment vs. the subsequent risks associated with advanced cancer. Cytotoxic chemotherapy is largely ineffective in treating prostate cancer. A combination of agents is no more effective than a single agent, and the addition of chemotherapy to hormonal therapy does not improve survival. Eisenberger, M. A., 1988, Chemotherapy for prostate carcinoma. In: Wittes, R. E., ed. *Consensus Development Conference on the Management of Clinically Localized Prostate Cancer.* NCI monographs No. 7 Washington D.C.: Government Printing Office: 151–153 (NIH publication no. 88-3005). Accordingly, there is a great demand for improved prostate cancer treatments.

The present invention provides a method of preclinical testing of AICA and/or 5-amino or a substituted amino 1,2,3-triazole organic and inorganic salts in experimental prostatic cancer models, for example, in the androgen-independent Dunning R-3327-AT-I rat prostatic cancer model (Pinski, J., et al., 1994, Int. J. Cancer 59:51–55; the high metastatic potential prostatic cancer model PC-3-M (Koziowski, J. M., et al., 1984, Cancer Res. 44:3522–3529) (See infra, Section 7); and the non-metastatic DU-145 prostatic cancer model (Karmali, R. A., et al., Anticancer Res. 7:1173–1180). The present invention also provides a method of treating prostate cancers comprising administering a salt of AICA or TRIAZOLES which prevents development of neoplastic cells, inhibits the proliferation and spread of cancer cells, stromal cells, and/or associated vascular endothelial cells and reduces the detrimental effects of toxicity caused by combination anti-cancer drugs.

6. EXAMPLE

Orotic Acid Salt of 5-amino-1-(4-[4-chlorobenzoyl]-3,5-dichlorobenzyl)-1,2,3-triazole-4-carboxamide 5-amino-1-(4-[4-chlorobenzoyl]-3,5-dichlorobenzyl)-1,2,3-triazole-4-carboxamide (L651582) was supplied by Merck Research Laboratories. Two grams of L651582 and 0.87 grams of orotic acid were added to a 30 ml water+120 ml methanol solution and heated to boiling for 15 min. The resulting clear solution was filtered through activated charcoal Norit. A white crystalline precipitate with M.P.234–235° C. weighing approximately 2 grams was formed upon cooling and drying. Analysis of crystals by proton NMR using deuterium labeled dimethylsulfoxide (DMSO) as the solvent indicated both orotate and L651582 in a ratio of approximately 1:2, with crystals of both compounds joined by ionic bands. See FIG. 1.

7. EXAMPLE

Prevention and/or Treatment of Neoplasia by the Administration of AICA or L651582 Salts In the examples that follow, the androgen-independent Dunning R-3327-AT-1 prostatic tumor model is used to demonstrate the prevention and/or treatment of prostatic tumors in vivo by treatment with L651582 or L651582 and AICA salts.

7.1 Cell Culture

The AT-1 androgen-independent prostatic cancer cells (supplied by the Prostate and Breast Laboratories of the Johns Hopkins Oncology Center) were grown in RPMI 1640 medium (Grand Island Biologicals) with L-glutamine+10% fetal calf serum (Hyclone Inc.) and dexamethasone 250 nM (Sigma Chem. Corp.). The cells were maintained in T-75 plastic flasks (Corning Glass). For inoculation, cells grown in T-75 flasks were detached at late log phase by trypsinization, and duplicate aliquots counted in an electronic particle counter (Coulter Model ZBI, Coulter Electronics). The cells were diluted in phosphate buffer saline and $0.8 \times 10^6$ cells/0.25 ml medium were injected subcutaneously in male Copenhagen rats (250–265 gms).

7.2. Treatment of Rats

Five groups of Copenhagen male rats (Harlan Sprague Dawley) (12 per group) were inoculated subcutaneously on the same day with $0.8 \times 10^6$ R-3327-AT-1 tumor cells. Each group included three rats which received no tumor cells but were monitored for body weight changes. Five days following tumor cell inoculation, the rats were injected subcutaneously with the test compounds dissolved in DMSO and later in a trioctanoin emulsion. Body weights and tumor size were recorded on a weekly basis. The five groups of rats were treated as follows: Group 1 rats were treated with 4-amino-5-imidazole carboxamide orotate at a dose of 10 mg/100 gm body weight; Group 2 rats were treated with 4-amino-5-imidazole carboxamide hydrochloride at a dose of 10 mg/100 gm body weight; Group 3 rats received L651582 at a dose of 2.6 mg/100 gm body weight; Group 4 rats received L651582 orotate at a dose of 2.6 mg/100 gm body weight; and Group 5 rats received the control vehicle DMSO or trioctanoin. These doses were selected based on observations that the orotate salt of 4-amino-5-imidazolecarboxamide (U.S. Pat. No. 3,271,398) and L651582 (Kohn, E. C. et al., 1990, J.Natl. Cancer Inst. 82:54–60) were not found to be toxic at these levels.

Rats were fed the NIH-07 stock diet throughout the experiment and received water ad libitum.

7.3 Results of Treatment

Animal weight gains did not differ among the 5 test groups over time both in the control and in the tumor-bearing rats.

Tumors became measurable in 3 dimensions at about 20 post-inoculation of tumor cells and then entered a phase of rapid exponential growth. Tumor volume and weight at necropsy were used as the outcome measures (Tables 1 and 2).

TABLE 1

TUMOR VOLUME (mm³)

| | | Volume = WxLxH/8)Xπ | | Volume = √WxVLxVH | |
|---|---|---|---|---|---|
| GROUP | N | MEAN | Std. Dev. | MEAN | Std. Dev. |
| 1 | 12 | 9993 | 9580 | 146 | 68 |
| 2 | 12 | 4882 | 3061 | 106 | 36 |
| 3 | 11 | 4720 | 2256 | 107 | 27 |
| 4 | 12 | 4077 | 1459 | 100 | 20 |
| 5 | 12 | 6995 | 4170 | 129 | 37 |

TABLE 2

TUMOR WEIGHT (gm)

| GROUP | N | MEAN | Std. Dev. |
|---|---|---|---|
| 1 | 12 | 7.42 | 4.95 |
| 2 | 12 | 4.95 | 2.90 |
| 3 | 11 | 5.31 | 2.17 |
| 4 | 12 | 4.48 | 1.49 |
| 5 | 12 | 6.31 | 3.09 |

Differences among the five groups were analyzed by ANOVA (P-O.0382). Briefly, AICA hydrochloride, L651582 and L651582 orotate inhibited the tumor growth as indicated by the mean tumor volume and tumor weight compared with the control group. The results obtained in the group treated with AICA orotate given subcutaneously were highly variable as evidenced by the large standard deviation. However, the tumors in this group had the least number of necrotic bleeding lesions.

The data obtained also demonstrate that the orotate salt of L651582 was more effective than the L651582 in reducing the tumor growth.

8. TREATMENT AND PREVENTION REGIMENS FOR PRIMARY AND METASTATIC NEOPLASMS BY ADMINISTRATION OF AICA HYDROCHLORIDE OR L651582 OROTATE

The invention is illustrated, by way of protocols for chemotherapy used in a patient suffering from cancer, which demonstrate the effectiveness of orazamide in the prevention and treatment of different cancers.

AICA salts and/or L651582 salts may be used in combination with a variety of chemotherapeutic drugs which produce cytotoxicity by interfering with a variety of cellular processes. The compositions of the present invention are useful in preventing the transformation of preneoplastic cells to tumor cells, and inhibiting tumor cell proliferation, invasion and metastasis.

The commonly used chemotherapeutic agents which can be employed with the AICA and/or L651582 salts according to the present invention include a variety of agents which are classified by their mode of action, origin or structure, although some drugs do not fit clearly into any single group. The categories include alkylating agents, antimetabolites, antibiotics, alkaloids and miscellaneous agents including hormones.

Alkylating agents (e.g., nitrogen mustard, cyclophosphamide, melphalan, busulfan, etc.) form covalent bonds with nucleic acids. These agents alter the integrity of DNA by transferring an alkyl group to the nucleic acids. Agents in this class have toxicities related to bone marrow depression, amenorrhea, male sterility, etc.

Antimetabolites (e.g., methotrexate, mercaptopurine, thioguanine, fluorouracil, etc.) are structurally similar to normal metabolic substrates. They impair cellular functions by substituting for normal precursors in vital physiologic reactions or by blocking these reactions. Agents in this class have toxicities related to bone marrow depression, liver damage, etc.

Antibiotics (e.g., doxorubicin, daunorubicin, bleomycin, etc.) are biologic products of bacteria and fungi. They do not share a single mechanism of action. For example, the anthracyclines, doxorubicin and daunorubicin achieve their cytotoxic effect by several mechanisms, including intercalation between DNA strands, production of free radicals, chelation of divalent cations and reaction with cell membranes. The wide range of potential sites of action may account for the broad efficacy as well as the toxicity of the anthracyclines. Myers, C. E., 1992, *Cancer Chemother. Biol. Response Modif.* 13:45.

Alkaloids (e.g., vincristine, vinblastine, vindesine, paclitaxel(taxol)) bind to the cytoplasmic structural protein tubulin and prevent the assembly or disassembly of microtubules. The neuropathy associated with the use of these drugs results from their action on microtubules in the long axons of nerves.

Miscellaneous agents have diverse actions. For example, dacarbazine and procarbazine (analogs of AICA) are similar in their modes of action to the alkylating agents. Asparaginase, on the other hand, acts enzymatically.

Hormones, particularly the steroid hormones (prednisone, progesterone, estrogen) and androgen, are frequently used in cancer therapy. Other hormones that play important roles in cancer management include tamoxifen, an antiestrogen used to treat breast cancer, and leuprolide, a human gonadotropin-releasing hormone analogue, which is employed in the treatment of breast cancer and prostate cancer.

It is believed that the administration of an effective dose of a salt of AICA or 5-amino or substituted amino 1,2,3-traizoles, e.g., AICA hydrochloride or L651582 orotate respectively, alone or in combination with each other or one or more of one of the above-discussed chemotherapeutic agents may completely inhibit and prevent the growth and/or spread of a variety of primary and secondary cancers in vivo in patients. When another chemotherapeutic agent is administered together with an AICA or 5-amino or substituted 1,2,3-triazole salt, it is administered according to protocols and dosage ranges known to those skilled in the art suitable for such chemotherapeutic agent.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A salt of a compound having the formula:

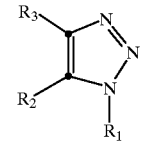

in which an organic acid is bonded to $R_2$ wherein:

$R_1$ is

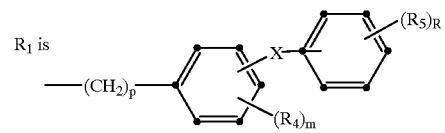

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; $R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atoms.

2. A salt of a compound having the formula:

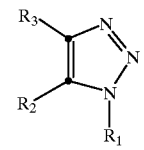

in which an inorganic acid is bonded to $R_2$ wherein:

$R_1$ is

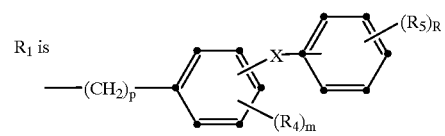

wherein p is 0 to 2; m is 0 to 4; and n is 0 to 5; X is O, S, SO, $SO_2$, CO, CHCN, $CH_2$ or $C=NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifluoromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; $R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atoms.

3. The salt according to claim 1 derived from a combination of the compound having the formula:

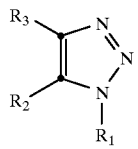

wherein

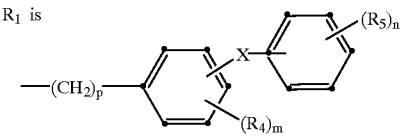

wherein p is 0 to 2; m is 0 to 4; and n is 0 to 5; X is O, S, SO, $SO_2$, CO, CHCN, $CH_2$ or C=$NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifuloromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; $R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atom, and an acid selected from the group consisting of orotic, lactic, succinic, maleic, citric, tartaric, gluconic and galactonic.

4. The salt according to claim 2 derived from a combination of the compound having the formula:

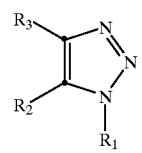

wherein:

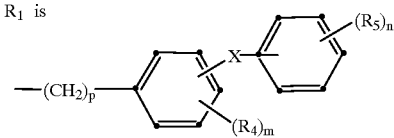

wherein p is 0 to 2; m is 0 to 4; and n is 0 to 5; X is O, S, SO, $SO_2$, CO, CHCN, $CH_2$ or C=$NR_6$ where $R_6$ is hydrogen, loweralkyl, hydroxy, loweralkoxy, amino, loweralkylamino, diloweralkylamino or cyano; and, $R_4$ and $R_5$ are independently halogen, cyano, trifluoromethyl, loweralkanoyl, nitro, loweralkyl, loweralkoxy, carboxy, lowercarbalkoxy, trifuloromethoxy, acetamido, loweralkylthio, loweralkylsulfinyl, loweralkylsulfonyl, trichlorovinyl, trifluoromethylthio, trifluoromethylsulfinyl, or trifluoromethylsulfonyl; $R_2$ is amino, mono or diloweralkyl amino, acetamido, acetimido, ureido, formamido, formimido or guanidino; and $R_3$ is carbamoyl, cyano, carbazoyl, amidino or N-hydroxycarbamoyl; wherein the loweralkyl, loweralkyl containing, loweralkoxy and loweralkanoyl groups contain from 1 to 3 carbon atoms, and an acid selected from the group consisting of hydrochloric and phosphoric.

5. The hydrochloride salt of 5-amino-1-(4-[4-chlorobenzoyl]-3,5-dichlorobenzyl)-1,2,3-triazole-carboxamide and hydrochloric acid.

6. The orotate salt of 5-amino-1-(4-[4-chlorobenzoyl]-3,5-dichlorobenzyl)-1,2,3-triazole-carboxamide and orotic acid.

7. The phosphate salt of 5-amino-1-(4-[4-chlorobenzoyl]-3,5-dichlorobenzyl)-1,2,3-triazole-carboxamide and phosphoric acid.

* * * * *